US009893438B1

(12) United States Patent
Oster et al.

(10) Patent No.: US 9,893,438 B1
(45) Date of Patent: Feb. 13, 2018

(54) ELECTRICAL CONNECTORS FOR HIGH DENSITY ATTACH TO STRETCHABLE BOARDS

(71) Applicant: Intel Corporation, Santa Clara, CA (US)

(72) Inventors: Sasha Oster, Chandler, AZ (US); Adel A. Elsherbini, Chandler, AZ (US); Feras Eid, Chandler, AZ (US); Aleksandar Aleksov, Chandler, AZ (US); Amit Sudhir Baxi, Bangalore (IN); Johanna M. Swan, Scottsdale, AZ (US); Vincent S. Mageshkumar, Navi Mumbai (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/281,814

(22) Filed: Sep. 30, 2016

(51) Int. Cl.

| | |
|---|---|
| ***A61B 17/00*** | (2006.01) |
| ***H01R 4/58*** | (2006.01) |
| ***H01R 43/26*** | (2006.01) |
| ***H01R 13/03*** | (2006.01) |
| ***A44B 17/00*** | (2006.01) |
| ***A44B 19/24*** | (2006.01) |

(52) U.S. Cl.
CPC .......... *H01R 4/58* (2013.01); *A44B 17/0041* (2013.01); *A44B 19/24* (2013.01); *H01R 13/03* (2013.01); *H01R 43/26* (2013.01)

(58) Field of Classification Search
CPC .... A61B 17/12; A61B 17/135; H05K 1/0306; A44B 18/0076
USPC .......... 606/203–204, 201; 361/749; 428/100; 439/285
See application file for complete search history.

(56) References Cited

U.S. PATENT DOCUMENTS

| | | | | |
|---|---|---|---|---|
| 4,067,342 | A | 1/1978 | Burton | |
| 4,259,965 | A | 4/1981 | Fukuda et al. | |
| 5,499,927 | A * | 3/1996 | Ohno | H01R 13/28 29/408 |
| 7,637,747 | B2 | 12/2009 | Jaatinen et al. | |
| 9,391,394 | B2 | 7/2016 | Kockx et al. | |
| 2006/0224067 | A1 | 10/2006 | Giftakis et al. | |
| 2006/0246744 | A1 | 11/2006 | Marmaropoulos et al. | |
| 2007/0100219 | A1 | 5/2007 | Sweitzer et al. | |
| 2008/0004515 | A1 | 1/2008 | Jennewine | |

(Continued)

FOREIGN PATENT DOCUMENTS

JP 06333648 A 12/1994

OTHER PUBLICATIONS

"U.S. Appl. No. 15/215,531, Non Final Office Action dated May 15, 2017", 13 pgs.

(Continued)

*Primary Examiner* — Phuong Chi T Nguyen
(74) *Attorney, Agent, or Firm* — Schwegman Lundberg & Woessner, P.A.

(57) ABSTRACT

A system can include a first portion of a fabric fastener, a second portion of the fabric fastener, wherein the first portion and the second portion are configured to mechanically connect with each other and to resist separation from each other once connected, and wherein the first and second portions include a plurality of corresponding electrical contacts configured to form a plurality of individual electrical connections when the first portion is mechanically connected with the second portion.

6 Claims, 7 Drawing Sheets

(56) References Cited

U.S. PATENT DOCUMENTS

| | | | |
|---|---|---|---|
| 2009/0054737 | A1 | 2/2009 | Magar et al. |
| 2009/0076363 | A1 | 3/2009 | Bly et al. |
| 2009/0076559 | A1 | 3/2009 | Libbus et al. |
| 2009/0131838 | A1 | 5/2009 | Fotiadis et al. |
| 2009/0182393 | A1 | 7/2009 | Bachinski |
| 2009/0203244 | A1 | 8/2009 | Den Toonder et al. |
| 2010/0136804 | A1 | 6/2010 | Strickland |
| 2012/0157807 | A1 | 6/2012 | Virtanen et al. |
| 2012/0238890 | A1 | 9/2012 | Baker et al. |
| 2012/0295451 | A1 | 11/2012 | Hyun-Jun et al. |
| 2013/0109937 | A1 | 5/2013 | Banet et al. |
| 2013/0166006 | A1 | 6/2013 | Williams |
| 2013/0273752 | A1 | 10/2013 | Rudisill et al. |
| 2014/0162468 | A1 | 6/2014 | Kim |
| 2015/0087949 | A1 | 3/2015 | Felix et al. |
| 2015/0150502 | A1 | 6/2015 | Wu |
| 2015/0303619 | A1 | 10/2015 | Kockx et al. |
| 2016/0099517 | A1 | 4/2016 | Fernandes et al. |
| 2016/0121098 | A1 | 5/2016 | Kockx et al. |
| 2016/0296159 | A1 | 10/2016 | Larson et al. |

OTHER PUBLICATIONS

"U.S. Appl. No. 15/216,502, Examiner Interview Summary dated Feb. 1, 2017", 3 pgs.

"U.S. Appl. No. 15/216,502, Non Final Office Action dated Dec. 15, 2016", 15 pgs.

"U.S. Appl. No. 15/216,502, Notice of Ailowance dated Apr. 5, 2017", 5 pgs.

"U.S. Appl. No. 15/216,502, Response filed Feb. 17, 2017 to Non Final Office Action dated Dec. 15, 2016", 11 pgs.

"International Application Serial No. PCT/US2016/040476, International Search Report dated Jan. 10, 2017", 4 pgs.

"International Application Serial No. PCT/US2016/040476, Written Opinion dated Jan. 10, 2017", 8 pgs.

"Listen to Your Heart Arrythmias", iRhythm Technologies, [Online], Retrieved from the Internet: <URL: http://www.irhythmtech.com/patients-heart-arrhythmias-afib.php, (Accessed Mar. 31, 2016), 5 pgs.

"SEEQ™ Mobile Cardiac Telemetry (MCT) Device", [Online]. Retrieved from the Internet; <URL: http://www.medtronicdiagnostics.com/us/cardiac-monitors/seeq-mct-system/seeq-mct-device/index.htm, (Accessed Mar. 31, 2016), 4 pgs.

Andrew. A. Kostrzewski, et al., "Innovative, wearable snap connector technology for Improved networking in electronic garments".

"U.S. Appl. No. 15/215,531, Notice of Allowance dated Dec. 15, 2017", 7 pgs.

"International Application Serial No. PCT/US2017/049159, International Search Report dated Dec. 11, 2017", 3 pgs.

"International Application Serial No. PCT/US2017/049159, Written Opinion dated Dec. 11, 2017", 7 pgs.

* cited by examiner

ELECTRICAL CONNECTORS FOR HIGH DENSITY ATTACH TO STRETCHABLE BOARDS

TECHNICAL FIELD

The disclosure herein relates generally to electrical connectors and more particularly to electrical connectors for flexible materials and stretchable traces.

BACKGROUND

Multiple terminal electrical connectors that exist today have fairly high z-height, are not necessarily compatible with electric substrates, and in many cases, are not intuitive in how to use, especially for the lay user. Existing multiple-terminal electrical connectors can also require careful alignment or fine manipulation for proper use. Examples of such electrical connectors include flex connectors, which can use pressure contact or a small "lever" to open and close the contact pins. Others include pin or socket type connectors where each individual connection can be re-made multiple times. Additionally, most of these connectors can not be easily attached to a stretchable boards or substrates such as a fabric. Existing wearable connectors for stretchable skin contact applications are mostly based on sophisticated snaps, conductive velcro or thread-through conductive rings. Sophisticated snaps can consume a large area on a device especially when several contacts are required. Additionally, sophisticated snaps can have relatively large Z-height which impacts fabricating devices that are discreet and that do not impact user comfort. Conductive Velcro can require relatively large area on the substrate which results in larger system size when several connections are needed. Conductive Velcro can not be easily designed to avoid user error (the user might assume that all the contacts are made when only one side is connected). Thread through conductive rings form permanent attachment and the threads must be cut to release the device which significantly complicates the attach and detach process for the user.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The present inventors have recognized electrical connectors that can be easily manipulated by the user. Such connectors can be discrete and very intuitive for the user to operate. The present inventors have recognized a need for such connectors as internet-of-things (IoT) systems have begun to emerge that have multiple components and that can benefit from detachable electrical connectors that are easily manipulated by a user. For example, systems are becoming more prevalent that contain both disposable and reusable electrical components. Such systems can include health monitoring systems that can contain a disposable part that is placed in continuous contact with the skin for measuring biosignals (ECG, respiration rate, etc) and is disposed of every few days due to skin shedding or desquamation. Alternatively, the disposable part may include a strip that receives a sample of blood or sweat from the user for chemical analysis and needs to be thrown away after each use. The reusable part may contain more expensive components that are not irreversibly impacted during use such as the processor, communication, or other sensor chips and/or a battery. These example systems can benefit from multiple-terminal electrical connectors that can be frequently attached or disconnected by the user without requiring sending the parts back to the vendor.

Figure 1A:
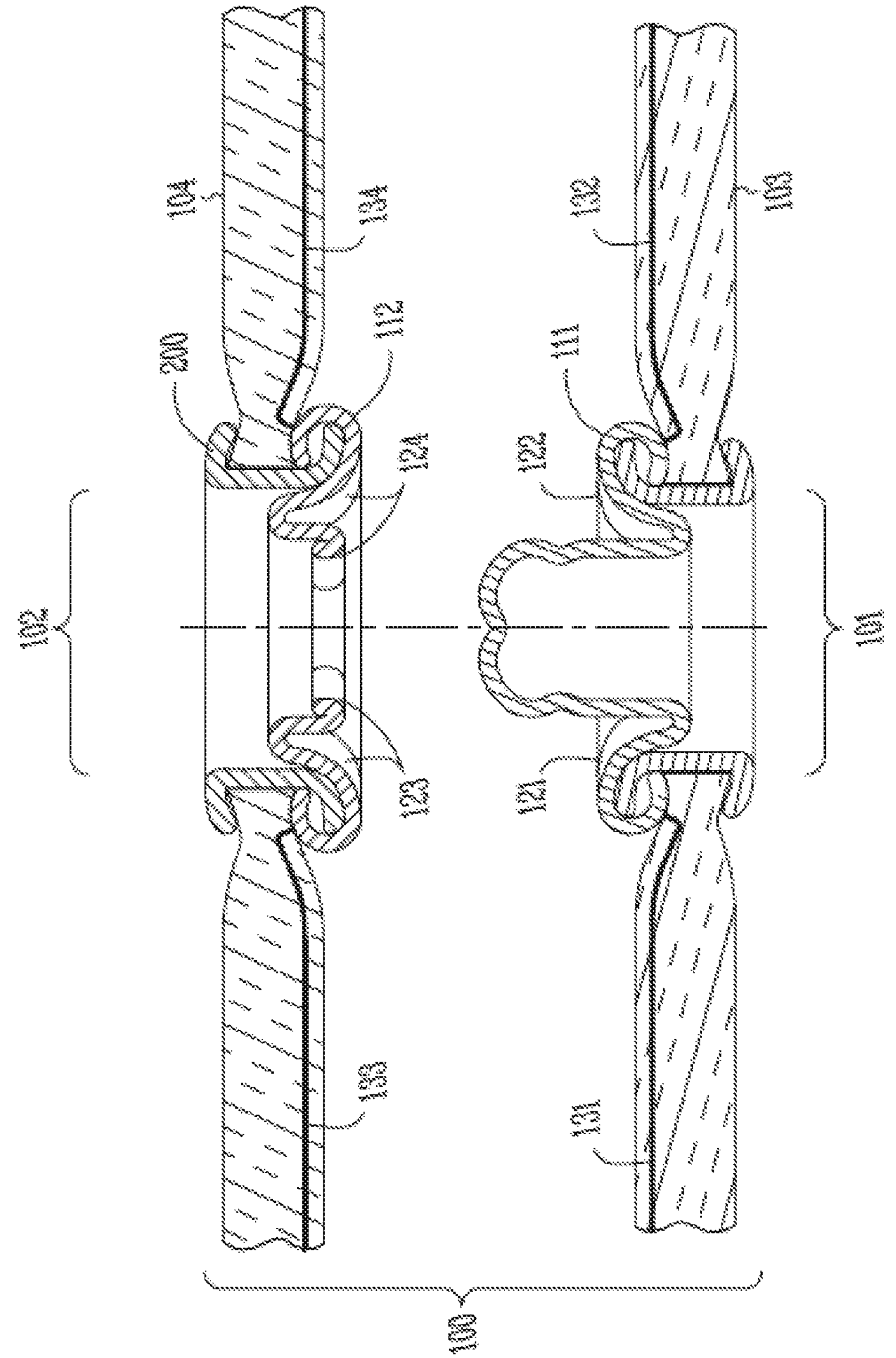
FIGS. 1A and 1B illustrates generally an example of a multiple-terminal snap connector 100 according to an example of the present subject matter.
Figure 1B:
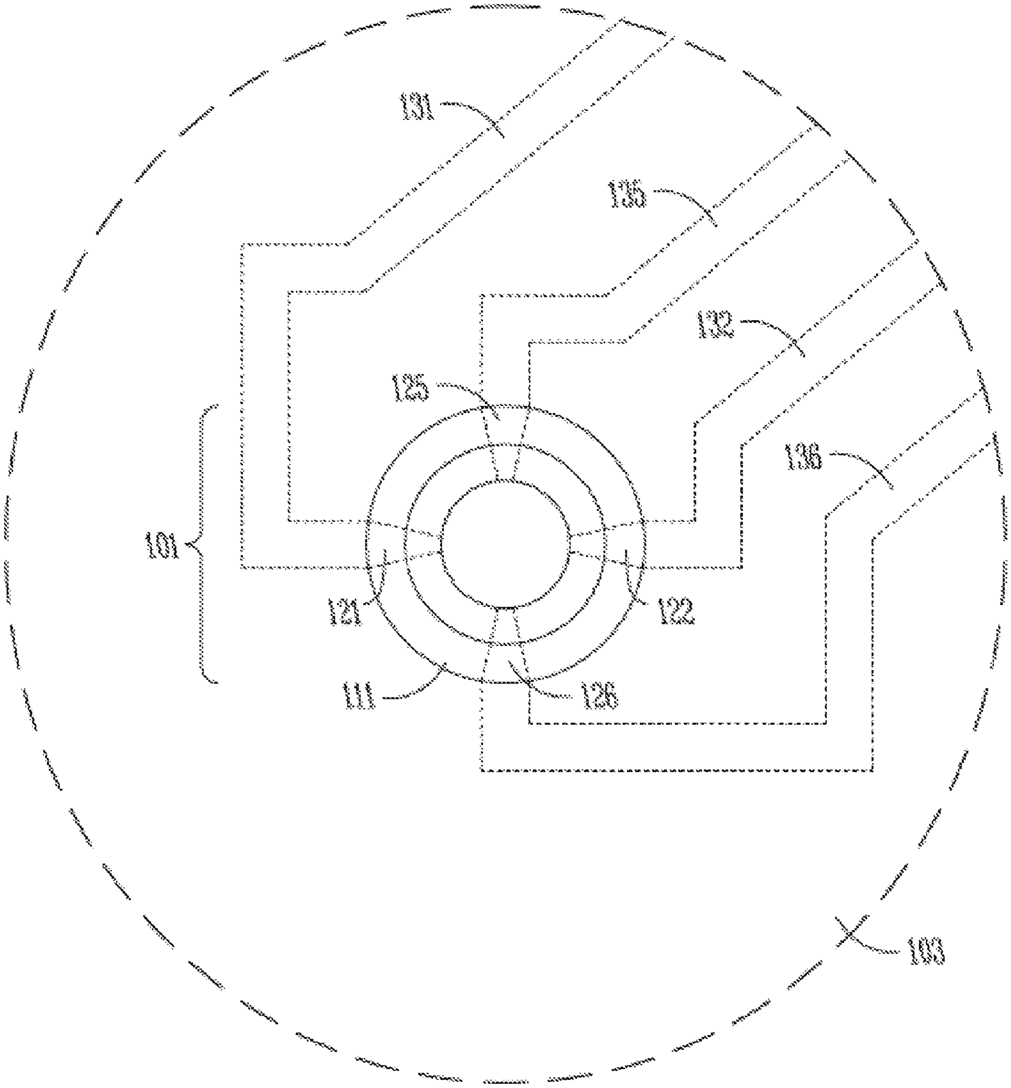

FIGS. 1A and 1B illustrates generally an example of a multiple-terminal snap connector 100 according to an example of the present subject matter. In general, a snap connector 100 for fabric can include a male portion or stud 101 and a female portion or socket 102 or receiver that can be mated together to mechanically connect two stretchable boards or substrates 103, 104 where at least one of the substrates is flexible such as a fabric, for example. The stud 101 and socket 102 are configured for easy mating and unmating, however, once mated, the stud 101 and socket 102 resist separation. In certain examples, each portion 101, 102 of the snap connector can include the connecting part 111, 112 and a prong part 113, or prong ring, that when used, or interfaced, together can fasten one half of the snap connector 100 to a flexible substrate 103, 104. In certain examples, a special tool can be used to assemble each half of a snap connector 100 with a flexible substrate 103, 104. The special tool can ensure that the prongs of the prong part 113 pierce the flexible substrate and engage and fold into the connecting part 111, 112 to hold the assembly fast to the substrate 103, 104.

In certain examples, each connection part of a snap connector can be patterned with an electrically conductive material to form an individual connector interface terminal 121, 122, 123, 124. Upon coupling the stud 101 with the socket 102, an electrical connection can be made between the connector interface terminals on each portion 101, 102 of the snap connector. In certain examples, the connecting part of each portion of the snap connector 100 can be assembled with the corresponding prong part such that each patterned terminal of the connecting part aligns with and couples to a corresponding trace 131, 132, 133, 134 or terminal of the flexible electronic substrate 103, 104. Upon mating with a corresponding connecting part, the snap connector 100 can facilitate multiple individual electrical connections between at least one flexible substrate 103 and a second substrate 104. In some examples, the structural material of each connecting part 111, 112 can be a non-conductive material. In certain examples, the structural material of each connecting part 111, 1112 can be a metallic material and the patterning process can include patterning an insulator material between the structural material and the conductive terminal material.

FIG. 1B illustrates generally a plan view of a stud portion 111 of a snap connector 100. The top-down view shows that additional connector interface terminals 125, 126 that can be patterned on the stud and can interface with corresponding traces of the substrate 103.

Figure 2:
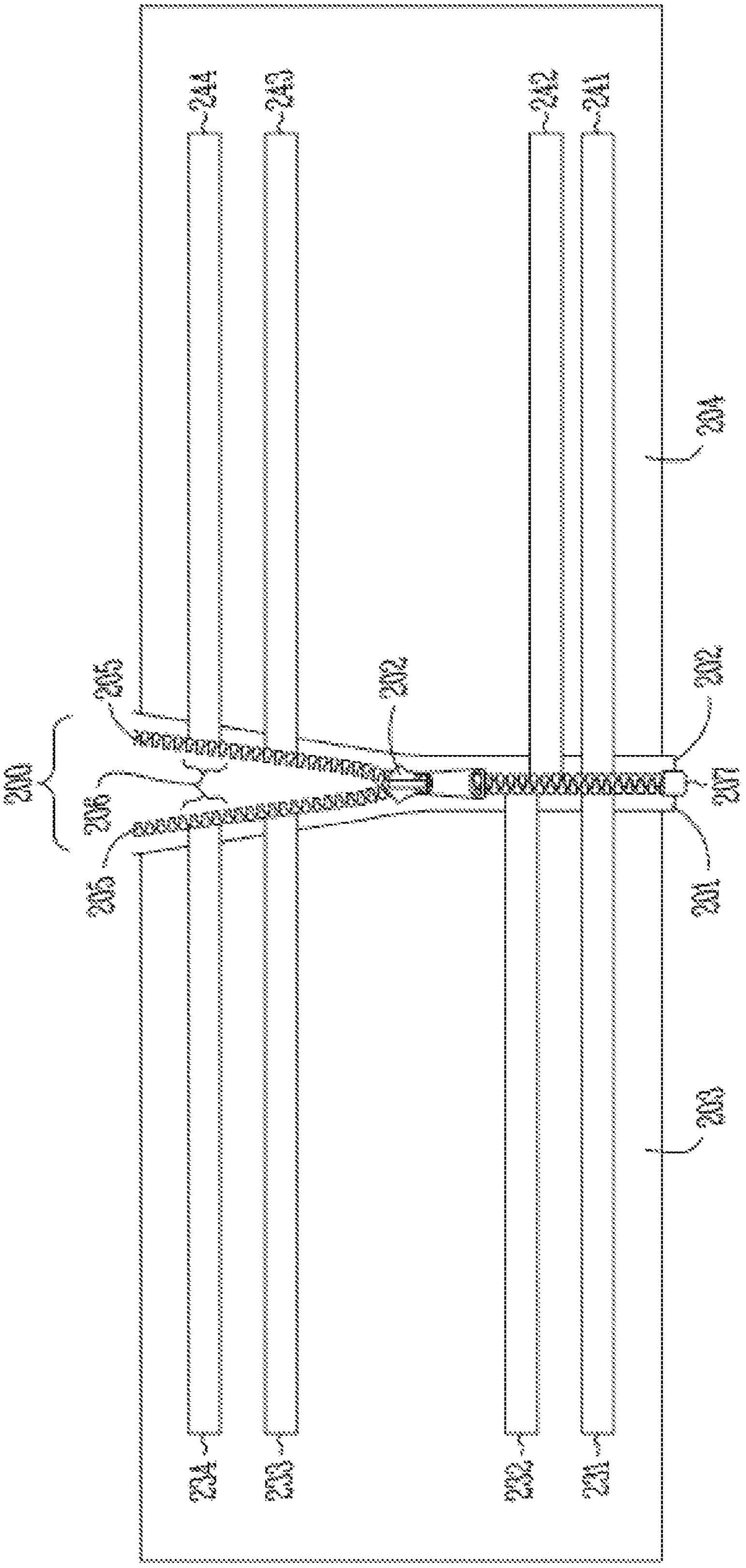
FIG. 2 illustrates generally a multiple terminal zipper connector 200 according to an example of the present subject matter.

FIG. 2 illustrates generally a multiple terminal zipper connector 200 according to an example of the present subject matter. The multiple terminal zipper connector 200 can include a first portion 201 and a second portion 202. At least one of the portions 201, 202 can be coupled to a flexible material 203, 204 such as a textile with integrated electrical traces 231, 232, 233, 234, 241, 242, 243, 244. Each portion 201, 202 can include fasteners, or teeth 205, configured to interlock with each other. The two plurality of teeth 205 that make op the portions 201, 202 of the multiple terminal zipper connector 200 may also be referred to as a chain. Some of the teeth 205, conductive teeth 206, can be electrically coupled to one of the electrical traces 231, 232, 233, 234, 241, 242, 243, 244 associated with a material coupled to the portion 201, 202 of the multiple terminal zipper connector 200, such as the flexible material discussed above. When the two portions 201, 202 of the multiple terminal zipper connector 200 are connected and corresponding conductive teeth 206 of each portion 201, 202 are interlocked, signals can be passed between the traces 231, 232, 233, 234, 241, 242, 243, 244 of each substrate associated with each portion 201, 202.

In certain examples, the first portion 201 can include a pin (not shown) and the second portion 202 can include a box 207, sometimes referred to as a retainer box, and a pull tab 208, zip mechanism or slider. The teeth 205 of the second portion 202 can be captured by the pull tab 208 and the pull tab 208 can slide along the teeth 205 of the second portion 202. To connect the two portions 201, 202, the pull tab 208 can be positioned adjacent the box 207 and the pin of the first portion 201 can be guided through the pull tab 208 into the box 207. The pull tab 208 can be slid along the teeth 205 of both the first and second portions 201, 202. As the pull tab 208 slides along the teeth 205, the pull tab 208 interlocks the teeth 205 of the first portion 201 with the teeth 205 of the second portion 202. Once the pull tab 208 is moved to the other end of the second portion 202, the two portions 201, 202 are completely connected. Multiple electrical connections, or terminations can be made when the two portions 201, 202 are zipped together by locating non-conductive teeth between each set of conductive teeth 206 of each portion 201, 202.

Moving the pull tab 208 through the interlocked teeth 205 can decoupled the first and second portions 201, 202. The multiple terminal zipper connector 200 can provide an easy to use electrical connector for systems that include disposable electronics, wearable electronics, fabric based electronics or combinations thereof.

In certain examples, a centerline of a first trace 232 on the first flexible material can be offset from the centerline of a second trace 242 of the second flexible material 204 and conductive teeth of the multiple terminal zipper connector 200 can electrically couple the first trace 232 with the second trace 242 when the conductive teeth are zipped together. In general, at least one of the first portion or the second portion of the multiple terminal zipper connector 200 can include a length of conductive teeth that is generally wider than one of the first trace 232 or the second trace 242. In certain examples, the ability to electrically couple offset traces can allow one portion 201, 202 of the multiple terminal zipper connector 200 to be used with multiple other portions where traces may need to terminate at different positions of the multiple terminal zipper connector 200.

Figure 3:
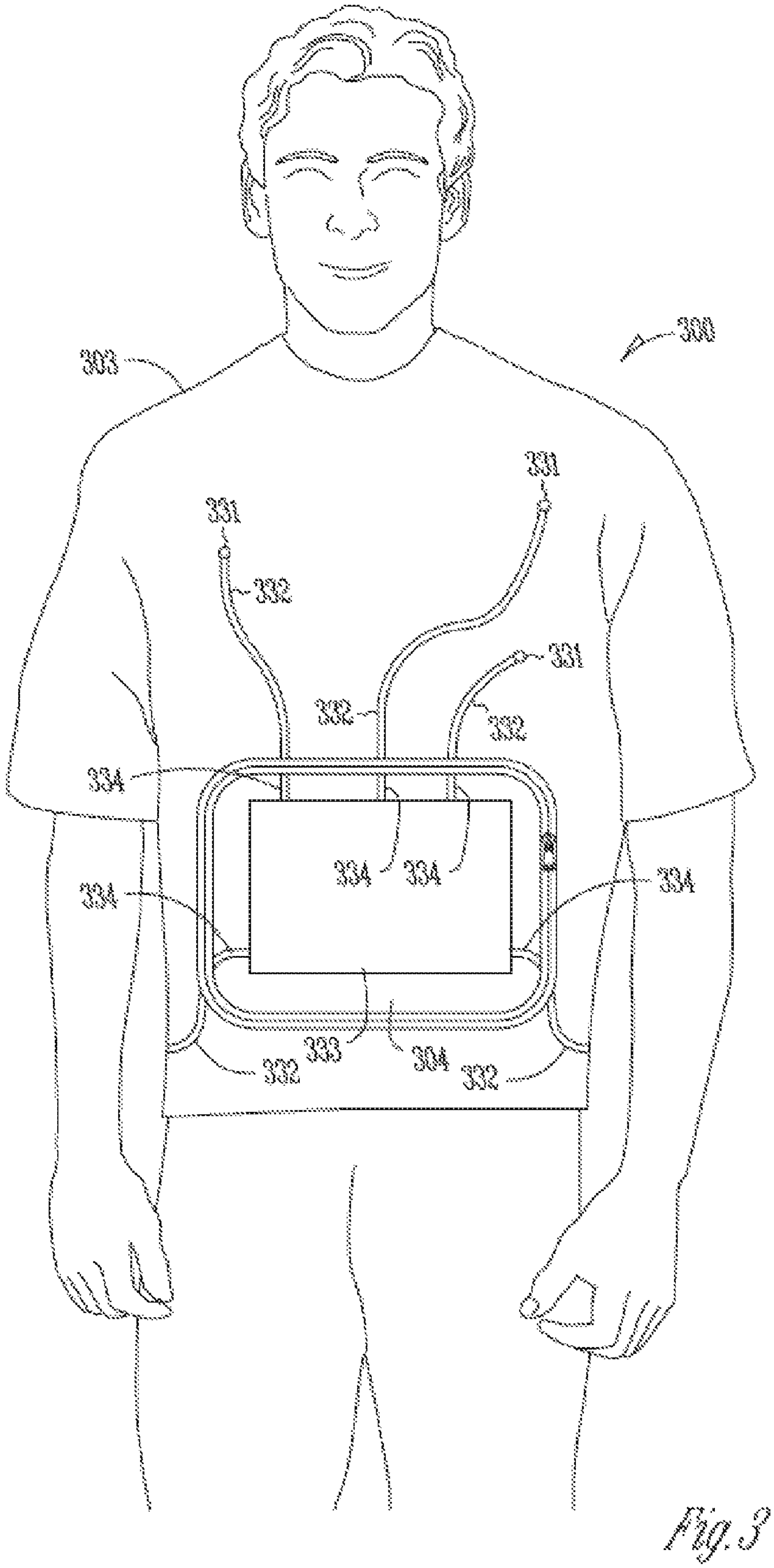
FIG. 3 illustrates generally a system 300 including a multiple terminal zipper connector 330.

FIG. 3 illustrates generally a system 300 including a multiple terminal zipper connector 330. The system 300 can include a first circuit 303 and a second circuit 304. In certain examples, the first circuit 303 can be in the form of a wearable circuit such as a shirt and can include a flexible substrate, a fabric substrate, a fabric-type substrate, such as a non-woven, or combinations thereof. In certain examples, the first circuit 303 can include one or more input or output devices 331, such as sensors, transducers, displays, keyboards or combinations thereof. The input or output devices 331 can be coupled to the multiple terminal zipper connector 330 via flexible traces 332 integrated with the substrate of the first circuit 303. In certain examples, the first circuit can include relatively low-cost devices such that the circuit is intended to be disposable, of limited use, or for one-time only use.

In certain examples, the second circuit 304 can include relatively more expensive devices and can be intended to be reused many times. The second circuit 304, for example, can include a controller 333 for interfacing with the devices 331 of the first circuit 303. The controller 333 can be coupled to the multiple terminal zipper connector 330 via flexible traces 334 integrated with the substrate of the second circuit 304. In certain examples, the second circuit 304 can include a flexible substrate, a fabric substrate, a fabric-type substrate.

In certain examples, the multiple terminal zipper connector can be used to electrically and mechanically couple the first circuit with the second circuit. As discussed above, when connected, multiple terminations of the second circuit can be electrically coupled with corresponding terminations of the first circuit via interlocking, conductive teeth of the multiple terminal zipper connector. Upon completion of a use of the system, the multiple terminal zipper connector can be disconnected using the pull tab and one or more of the first circuit and the second circuit can be quickly and easily connected for subsequent use with a corresponding circuit.

The illustrated example shows a multiple terminal zipper connector following a perimeter path about the substrate of the second circuit. It is understood that other paths are possible for coupling the first and second circuits using a multiple terminal zipper connector without departing from the scope of the present subject matter. In certain examples, the second circuit can include a pouch with one or more additional electrical connectors. In some examples, the pouch can be configured to hold different controllers and the connectors can be configured to couple the different controllers to corresponding input and output devices of a corresponding first circuit. In some examples, the second circuit processing logic is integrated with the pouch and the pouch and connectors are configured to hold expendable components such a power sources or memory devices that can easily be exchanged when such devices are expended, for example, by being depleted of most power or filling upto near capacity.

Figure 4:
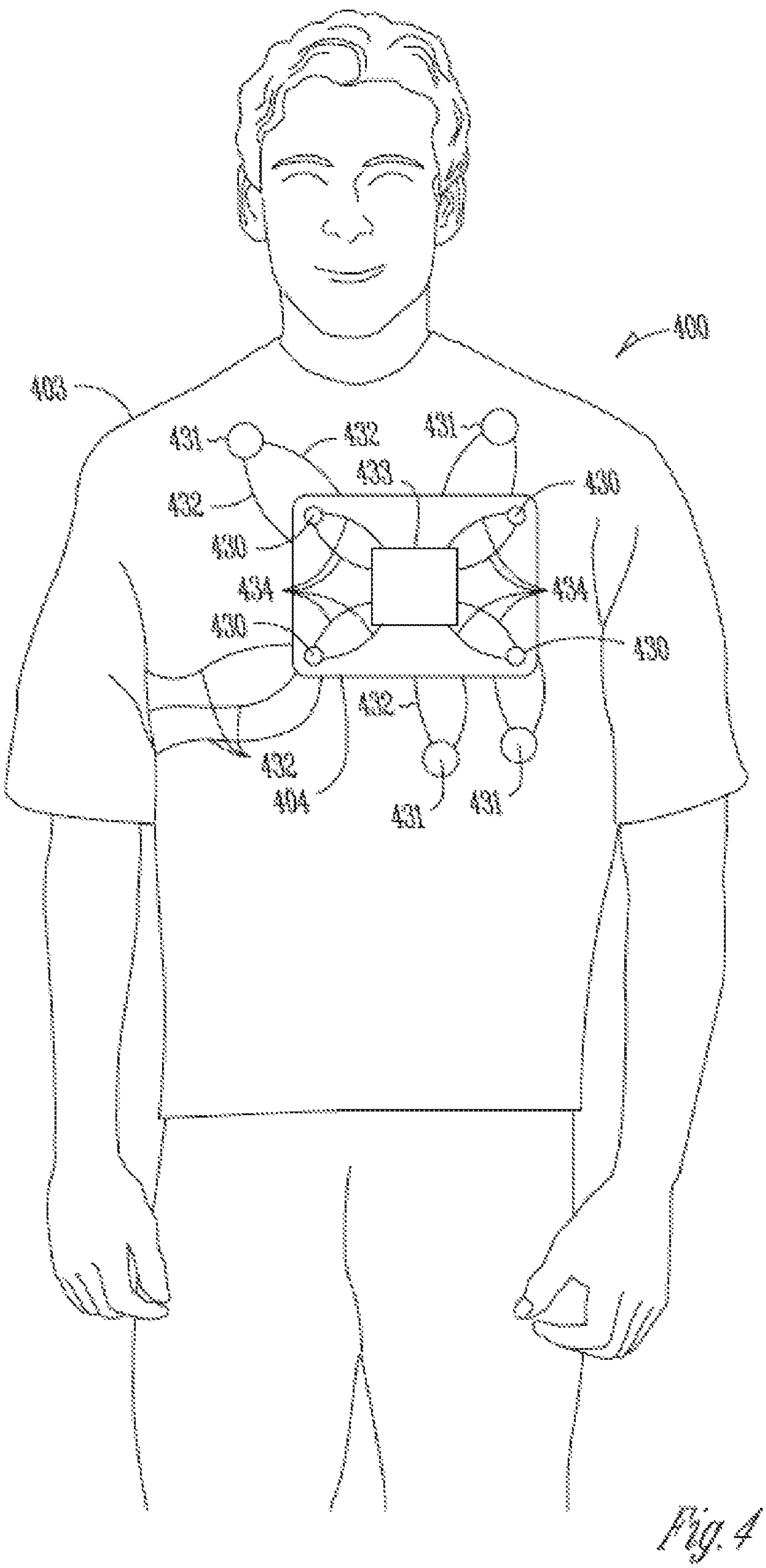
FIG. 4 illustrates generally a system including a multiple terminal snap fastener or connector 200.

FIG. 4 illustrates generally a system including a multiple terminal snap fastener or connector 200. The system can include a first circuit and a second circuit. In certain examples, the first circuit can be in the form of a wearable circuit such as a shirt and can include a flexible substrate, a fabric substrate, a fabric-type substrate, such as a non-woven, or combinations thereof. In certain examples, the first circuit can include one or more input or output devices, such as sensors, transducers, displays, keyboards or combinations thereof. In certain examples, the first circuit can include relatively low-cost devices such that the circuit is intended to be disposable, of limited use, or for one-time only use.

In certain examples, the second circuit can include relatively more expensive devices and can be intended to be reused many times. The second circuit for example can include a controller for interfacing with the devices of the first circuit. In certain examples, the second circuit can include a flexible substrate, a fabric substrate, a fabric-type substrate or combinations thereof.

In certain examples, the multiple terminal snap fasteners can be used to electrically and mechanically couple the first circuit with the second circuit. As discussed above, when connected, multiple terminations of the second circuit can be electrically coupled with corresponding terminations of the first circuit via the patterned interface of the receiver and stud of the snap fastener. Upon completion of a use of the system, the multiple terminal snap fasteners can be pulled apart to be disconnected and one or more of the first circuit and the second circuit can be quickly and easily connected for subsequent use with a corresponding circuit.

The illustrated example shows several multiple terminal snap fasteners at a perimeter about the substrate of the second circuit. It is understood that other locations are possible for coupling the first and second circuits using multiple terminal snap fasteners without departing from the scope of the present subject matter. In certain examples, the second circuit can include a pouch with one or more additional electrical connectors. In some examples, the pouch can be configured to hold different controllers and the connectors can be configured to couple the different controllers to different combinations of input and out devices of a corresponding first circuit. In some examples, the second circuit processing logic is integrated with the pouch and the pouch and snap fasteners are configured to hold expendable components such power sources or memory devices that can easily be exchanged when such devices are expended, for example, by being depleted of most power or filling up to near capacity.

Figure 5A:
FIGS. 5A-5C illustrate generally flowcharts of methods for coupling traces of stretchable boards or substrates together.
Figure 5B:
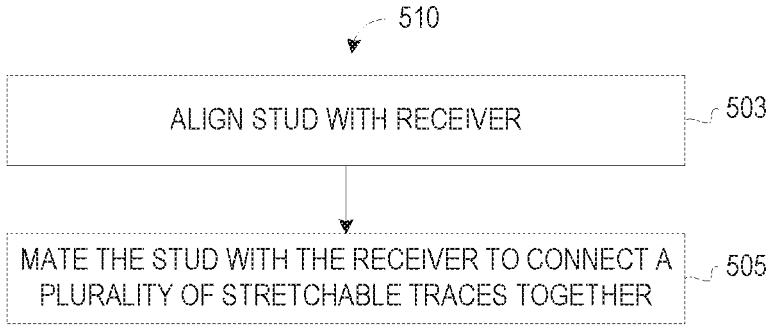
Figure 5C:
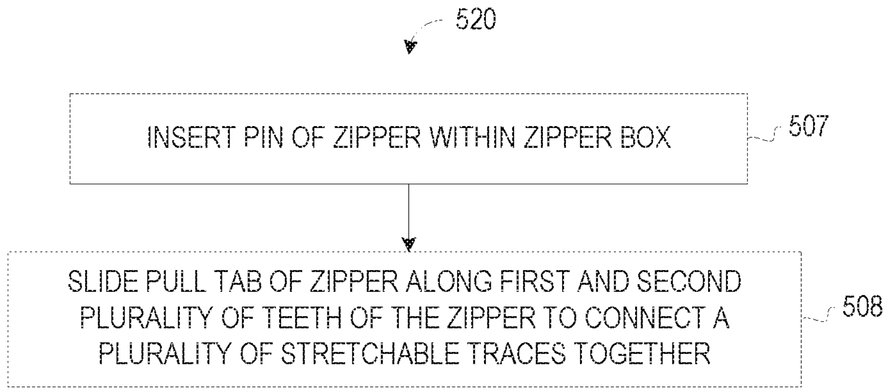

FIGS. 5A-5C illustrate generally flowcharts of methods for coupling traces of stretchable boards or substrates together. In certain examples, a method 500 for coupling traces of stretchable boards or substrates together and include, at 501, electrically coupling a plurality of stretchable traces together using a fabric fastener. In certain examples, the fabric fastener mechanically couples the fabrics together while simultaneously coupling the stretchable traces electrically. In certain examples, a method 510 for coupling traces of stretchable boards or substrates together can include, at 503, aligning a stud of a snap fastener with a receiver of the snap fastener, or vice versa, and, at 505, mating the stud with the receiver to connect the plurality of stretchable traces. In certain examples, a method 520 for coupling traces of stretchable boards or substrates together can include, at 507, inserting a pin of a zipper within a zipper box, and at 508, sliding the pull tab of the zipper along the teeth of the zipper to connect a plurality of stretchable traces together.

Figure 6:
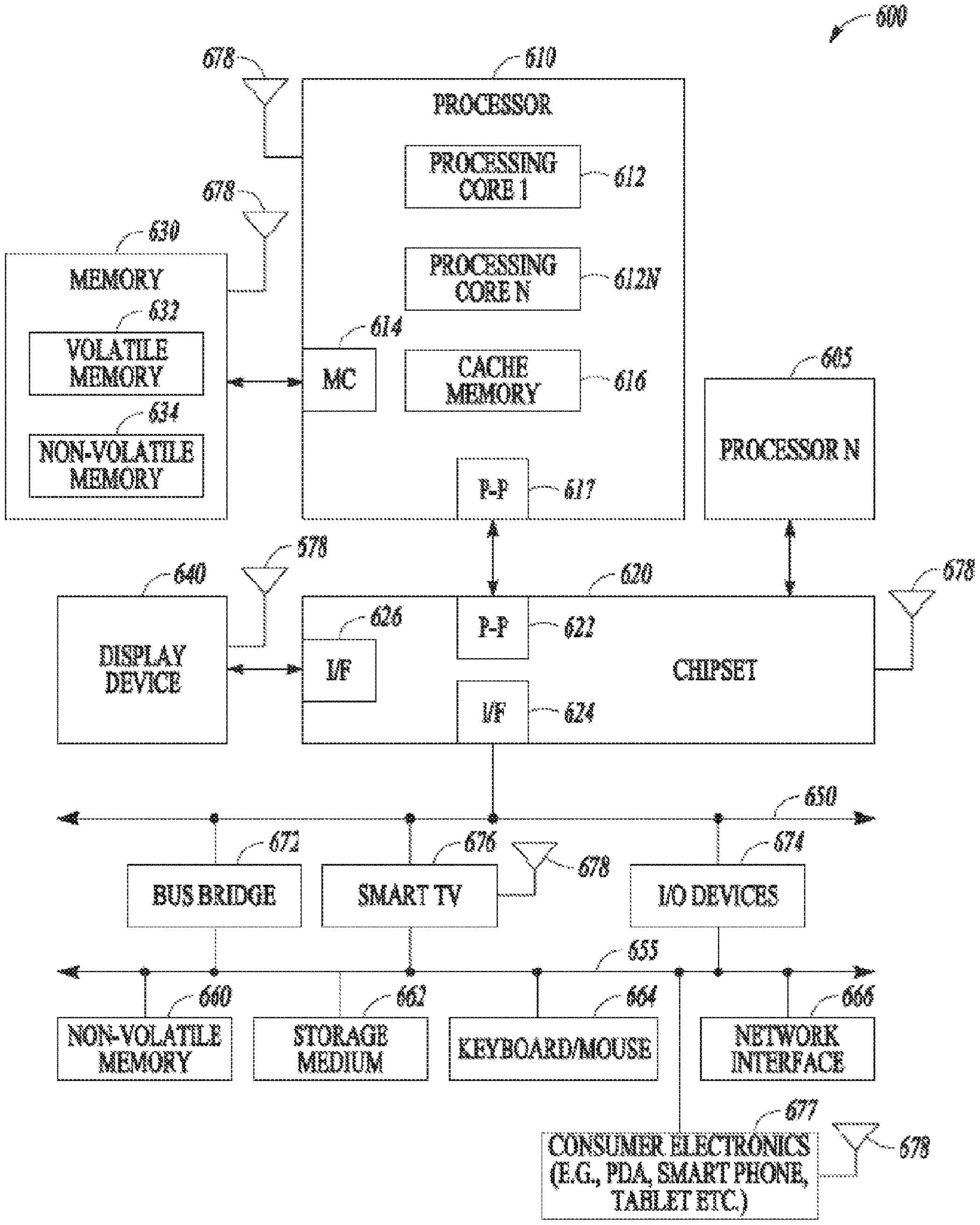
FIG. 6 illustrates a system level diagram, according to an embodiment of the present subject matter.

FIG. 6 illustrates a system level diagram, according to an embodiment of the present subject matter. For instance, FIG. 6 depicts an example of an electronic device (e.g., system) including a multiple-terminal snap connector as described above. FIG. 6 is included to show an example of a higher level device application for the present subject matter. In one embodiment, system 600 includes, but is not limited to, a desktop computer, a laptop computer, a netbook, a tablet, a notebook computer, a personal digital assistant (PDA), a server, a workstation, a cellular telephone, a mobile computing device, a smart phone, an Internet appliance or any other type of computing device. In some embodiments, system 600 is a system on a chip (SOC) system.

In one embodiment, processor 610 has one or more processing cores 612 and 612N, where 612N represents the Nth processor core inside processor 610 where N is a positive integer. In one embodiment, system 600 includes multiple processors including 610 and 605, where processor 605 has logic similar or identical to the logic of processor 610. In some embodiments, processing core 612 includes, but is not limited to, pre-fetch logic to fetch instructions, decode logic to decode the instructions, execution logic to execute instructions and the like. In some embodiments, processor 610 has a cache memory 616 to cache instructions and/or data for system 600. Cache memory 616 may be organized into a hierarchal structure including one or more levels of cache memory.

In some embodiments, processor 610 includes a memory controller 614, which is operable to perform functions that enable the processor 610 to access and communicate with memory 630 that includes a volatile memory 632 and/or a non-volatile memory 634. In some embodiments, processor 610 is coupled with memory 630 and chipset 620. Processor 610 may also be coupled to a wireless antenna 678 to communicate with any device configured to transmit and/or receive wireless signals. In one embodiment, the wireless antenna interface 678 operates in accordance with, but is not limited to, the IEEE 802.11 standard and its related family, Home Plug AV (HPAV), Ultra Wide Band (UWB), Bluetooth, WiMax, or any form of wireless communication protocol.

In some embodiments, volatile memory 632 includes, but is not limited to, Synchronous Dynamic Random Access Memory (SDRAM), Dynamic Random Access Memory (DRAM), RAMBUS Dynamic Random Access Memory (RDRAM), and/or any other type of random access memory device. Non-volatile memory 634 includes, but is not limited to, flash memory, phase change memory (PCM), read-only memory (ROM), electrically erasable programmable read-only memory (EEPROM), or any other type of non-volatile memory device.

Memory 630 stores information and instructions to be executed by processor 610. In one embodiment, memory 630 may also store temporary variables or other intermediate information while processor 610 is executing instructions. In the illustrated embodiment, chipset 620 connects with processor 610 via Point-to-Point (PtP or P-P) interfaces 617 and 622. Chipset 620 enables processor 610 to connect to other elements in system 600. In some embodiments of the invention, interfaces 617 and 622 operate in accordance with a PtP communication protocol such as the Intel® QuickPath Interconnect (CPI) or the like. In other embodiments, a different interconnect may be used.

In some embodiments, chipset 620 is operable to communicate with processor 610, 605N, display device 640, and other devices 672, 676, 674, 660, 662, 664, 666, 677, etc. Chipset 620 may also be coupled to a wireless antenna 678 to communicate with any device configured to transmit and/or receive wireless signals.

Chipset 620 connects to display device 640 via interface 626. Display 640 may be, for example, a liquid crystal display (LCD), a plasma display, cathode ray tube (CRT)

display, or any other form of visual display device. In some embodiments of the invention, processor 610 and chipset 620 are merged into a single SOC. In addition, chipset 620 connects to one or more buses 650 and 655 that interconnect various elements 674, 660, 662, 664, and 666. Buses 650 and 655 may be interconnected together via a bus bridge 672. In one embodiment, chipset 620 couples with a non-volatile memory 660, a mass storage device(s) 662, a keyboard/mouse 664, and a network interface 666 via interface 624 and/or 604, smart TV 676, consumer electronics 677, etc.

In one embodiment, mass storage device 662 includes, but is not limited to, a solid state chive, a hard disk drive, a universal serial bus flash memory drive, or any other form of computer data storage medium. In one embodiment, network interface 666 is implemented by any type of well known network interface standard including, but not limited to, an Ethernet interface, a universal serial bus (USB) interface, a Peripheral Component Interconnect (PCI) Express interface, a wireless interface and/or any other suitable type of interface. In one embodiment, the wireless interface operates in accordance with, but is not limited to, the IEEE 802.11 standard and its related family, Home Plug AV (HPAV), Ultra Wide Band (UWB), Bluetooth, WiMax, or any form of wireless communication protocol.

While the modules shown in FIG. 6 are depicted as separate blocks within the system 600, the functions performed by some of these blocks may be integrated within a single semiconductor circuit or may be implemented using two or more separate integrated circuits. For example, although cache memory 616 is depicted as a separate block within processor 610, cache memory 616 (or selected aspects of 616) can be incorporated into processor core 612.

ADDITIONAL EXAMPLES AND NOTES

Each of these non-limiting examples can stand on its own, or can be combined with one or more of the other examples in any permutation or combination.

In Example 1, a system can include a first portion of a fabric fastener, a second portion of the fabric fastener, wherein the first portion and the second portion are configured to mechanically connect with each other and to resist separation from each other once connected, and wherein the first and second portions include a plurality of corresponding electrical contacts configured to form a plurality of individual electrical connections when the first portion is mechanically connected with the second portion.

In Example 2, the fabric fastener of Example 1 optionally is a snap fastener, the first portion can include a stud and a first prong ring interfaced with the stud.

In Example 3, the second portion of any one or more of Examples 1-2 optionally includes a receiver and a second prong ring interfaced with the receiver.

In Example 4, the system of any one or more of Examples 1-3 optionally includes a first fabric assembly, a first circuit integrated with the first fabric assembly, and wherein the first fabric assembly is secured between the stud and the first prong ring.

In Example 5, a first trace of the first circuit and the first fabric assembly of any one or more of Examples 1-4 optionally is electrically coupled to a first conductive portion of the stud, the first conductive portion of the stud of any one or more of Examples 1-4 optionally includes a first portion of a first contact of the plurality of corresponding contacts.

In Example 6, the system of any one or more of Examples 1-5 optionally includes a second fabric assembly, a second circuit integrated with the second fabric assembly, and wherein the second fabric assembly is secured between the receiver and the second prong ring.

In Example 7, a first trace of the second circuit and the second fabric assembly of any one or more of Examples 1-6 optionally is electrically coupled to a first conductive portion of the receiver, the first conductive portion of the receiver of any one or more of Examples 1-4 optionally includes a second portion of the first contact of the plurality of corresponding contacts In Example 8, a second trace of the first circuit and the first fabric assembly of any one or more of Examples 1-7 optionally is electrically coupled to a second conductive portion of the stud, the second conductive portion of the stud of any one or more of Examples 1-4 optionally includes a first portion of a second contact of the plurality of corresponding contacts, and a second trace of the second circuit and the second fabric assembly of any one or more of Examples 1-7 optionally is electrically coupled to a second conductive portion of the receiver, the second conductive portion of the receiver of any one or more of Examples 1-7 optionally includes a second portion of the second contact of the plurality of corresponding contacts In Example 9, the fabric fastener of any one or more of Examples 1-8 optionally is a zipper, the zipper including a chain and a slider configured to mate and to separate teeth of the chain, wherein the first portion includes a first plurality of teeth of the chain, and wherein the second portion includes a second plurality of teeth of the chain.

In Example 10, the system of any one or more of Examples 1-9 optionally includes a first fabric assembly and a first circuit integrated with the first fabric assembly, wherein a first trace of the first circuit and the first fabric assembly is electrically coupled to a first plurality of conductive teeth of the first plurality of teeth, the first plurality of conductive teeth comprising a first portion of a first contact of the plurality of corresponding contacts In Example 11, the system of any one or more of Examples 1-10 optionally includes a second fabric assembly and a second circuit integrated with the second fabric assembly, wherein a first trace of the second circuit and the second fabric assembly is electrically coupled to a first plurality of conductive teeth of the second plurality of teeth, the first plurality of conductive teeth of the second plurality of teeth comprising a second portion of the first contact of the plurality of corresponding contacts.

In Example 12, when the first plurality of teeth are mated with the second plurality of teeth, the first trace of the first circuit of any one or more of Examples 1-11 optionally is electrically coupled to a first trace of the second circuit and the first trace of the first circuit is not aligned with the first race of the second circuit.

In Example 13, a second trace of the first circuit and the first fabric assembly of any one or more of Examples 1-12 optionally is electrically coupled to a second plurality of conductive teeth of the first plurality of teeth, the second plurality of conductive teeth comprising a first portion of a second contact of the plurality of corresponding contacts, and a second trace of the second circuit and the second fabric assembly of any one or more of Examples 1-12 optionally is electrically coupled to a second plurality of conductive teeth of the second plurality of teeth, the second plurality of conductive teeth of the second plurality of teeth comprising a second portion of the second contact of the plurality of corresponding contacts.

In Example 14, a method can include electrically coupling a plurality of stretchable traces of a first circuit with a corresponding plurality of stretchable traces of a second circuit using a fabric fastener, wherein the first circuit is integrated with a first fabric assembly; the first fabric assembly including a first portion of the fabric fastener, and wherein the second circuit is integrated with a second fabric assembly, the second fabric assembly including a second portion of the fabric fastener.

In Example 15, the first portion of any one or more of Examples 1-14 optionally includes a stud of a snap fastener and the second portion include a receiver of the snap fastener, and the electrically coupling a plurality of stretchable traces of any one or more of Examples 1-14 optionally includes aligning a stud of the fabric fastener with a receiver of the fabric fastener and mating the stud with the receiver.

In Example 16, the first portion of any one or more of Examples 1-15 optionally includes a first plurality of teeth of a chain of a zipper fastener and the second portion includes a second plurality of teeth of the zipper fastener, the electrically coupling a plurality of stretchable traces of any one or more of Examples 1-15 optionally includes inserting a pin associated with the second plurality of teeth within a slider integrated with the first plurality of teeth and within a retainer box and simultaneously sliding the slider along the first plurality of teeth and the second plurality of teeth away from the pin and the retainer box.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are legally entitled.

What is claimed is:

1. A snap fastener system comprising:

a first portion of a snap fastener, the first portion comprising:

a stud; and a first prong ring configured to interfaced with the stud and to capture fabric of a first fabric assembly between a portion of the stud and the first prong ring when interfaced;

a second portion of the snap fastener, the second portion comprising, a receiver; and a second prong ring configured to interfaced with the receiver and to capture fabric of a second fabric assembly between a portion of the receiver and the first prong ring when interfaced;

wherein the first portion and the second portion are configured to mechanically connect with each other and to resist separation from each other once connected; and wherein the first and second portions include a plurality of corresponding electrical contacts configured to form a plurality of individual electrical connections when the first portion is mechanically connected with the second portion.

2. The system of claim 1, including the first fabric assembly; and a first circuit integrated with the first fabric assembly.

3. The system of claim 2, wherein a first trace of the first circuit and the first fabric assembly is electrically coupled to a first conductive portion of the stud, the first conductive portion of the stud comprising a first portion of a first contact of the plurality of corresponding contacts.

4. The system of claim 3, including the second fabric assembly; and a second circuit integrated with the second fabric assembly.

5. The system of claim 4, wherein a first trace of the second circuit and the second fabric assembly is electrically coupled to a first conductive portion of the receiver, the first conductive portion of the receiver comprising a second portion of the first contact of the plurality of corresponding contacts.

6. The system of claim 5, wherein a second trace of the first circuit and the first fabric assembly is electrically coupled to a second conductive portion of the stud, the second conductive portion of the said comprising a first portion of a second contact of the plurality of corresponding contacts; and wherein a second trace of the second circuit and the second fabric assembly is electrically coupled to a second conductive portion of the receiver, the second conductive portion of the receiver comprising a second portion of the second contact of the plurality of corresponding contacts.

* * * * *